United States Patent
Ekre et al.

(10) Patent No.: US 9,480,701 B2
(45) Date of Patent: *Nov. 1, 2016

(54) LOW ANTICOAGULANT HEPARINS

(71) Applicant: DILAFORETTE AB, Solna (SE)

(72) Inventors: Hans-Peter Ekre, Stockholm (SE); Ulf Lindahl, Uppsala (SE); Erik Holmer, Stockholm (SE); Per-Olov Eriksson, Strängnäs (SE); Anna Leitgeb, Saltsjöbaden (SE); Mats Wahlgren, Stocksund (SE); Stefania Tiddia, Modena (IT); Lino Liverani, Faenza (IT)

(73) Assignee: DILAFORETTE AB, Solna (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/366,570

(22) PCT Filed: Dec. 19, 2012

(86) PCT No.: PCT/SE2012/051428
§ 371 (c)(1),
(2) Date: Jun. 18, 2014

(87) PCT Pub. No.: WO2013/095276
PCT Pub. Date: Jun. 27, 2013

(65) Prior Publication Data
US 2015/0031638 A1  Jan. 29, 2015

(51) Int. Cl.
*A61K 31/727* (2006.01)
*C08B 37/00* (2006.01)
*A61K 45/06* (2006.01)

(52) U.S. Cl.
CPC .............. *A61K 31/727* (2013.01); *A61K 45/06* (2013.01); *C08B 37/0063* (2013.01); *C08B 37/0075* (2013.01); *C08B 37/0078* (2013.01)

(58) Field of Classification Search
CPC .......... C08B 37/0063; C08B 37/0075; C08B 37/0078; A61K 45/06; A61K 31/727
USPC ........................................... 514/25; 536/17.5
See application file for complete search history.

(56) References Cited

U.S. PATENT DOCUMENTS

| | | | |
|---|---|---|---|
| 4,303,651 A | 12/1981 | Lindahl et al. | |
| 4,990,502 A | 2/1991 | Lormeau et al. | |
| 5,250,519 A | 10/1993 | Conrad et al. | |
| 5,280,016 A | 1/1994 | Conrad et al. | |
| 5,472,953 A | 12/1995 | Ekre et al. | |
| 5,527,785 A | 6/1996 | Bevilacqua et al. | |
| 5,767,269 A | 6/1998 | Hirsh et al. | |
| 5,993,810 A | 11/1999 | Lebovitz | |
| 6,028,061 A | 2/2000 | Bernfield et al. | |
| 6,486,137 B1 | 11/2002 | Lundqvist et al. | |
| 6,569,840 B1 * | 5/2003 | Yamashina | C08B 37/0075 514/56 |
| 6,596,705 B1 | 7/2003 | Varki et al. | |
| 8,071,569 B2 | 12/2011 | Mousa | |
| 2005/0075314 A1 | 4/2005 | Ekman-Ordeberg et al. | |
| 2005/0215519 A1 | 9/2005 | Viskov et al. | |
| 2006/0040896 A1 | 2/2006 | Kennedy | |
| 2006/0147415 A1 | 7/2006 | Mousa et al. | |
| 2007/0021378 A1 * | 1/2007 | Varki | A61K 31/727 514/56 |
| 2010/0298263 A1 | 11/2010 | Casu et al. | |
| 2010/0316640 A1 | 12/2010 | Sundaram et al. | |
| 2010/0324276 A1 * | 12/2010 | Sundaram | A61K 31/727 536/21 |
| 2011/0200673 A1 | 8/2011 | Mousa | |
| 2011/0206770 A1 * | 8/2011 | Mooney | A61K 9/2866 424/489 |

FOREIGN PATENT DOCUMENTS

| | | | |
|---|---|---|---|
| EP | 0735050 A2 * | 10/1996 | ............. C08B 37/10 |
| EP | 0867452 A1 | 10/1997 | |
| EP | 1059304 A1 | 12/2000 | |
| EP | 0735050 B1 * | 9/2002 | ............. C08B 37/10 |
| UA | 21707 | 3/2007 | |
| WO | 92/02232 A1 | 2/1992 | |
| WO | 94/08595 A1 | 4/1994 | |
| WO | 03/055499 A1 | 7/2003 | |
| WO | 03/088980 A1 | 10/2003 | |
| WO | 2007/014155 A2 | 2/2007 | |
| WO | 2009007224 A1 | 1/2009 | |
| WO | 2009059284 A2 | 5/2009 | |

(Continued)

OTHER PUBLICATIONS

Leitgeb et al, Am. J. Trop. Med. Hyg. 2011, 8493, 390-96.*
Hjelm Cluff et al., "Prolonged Labour Associated with Lower Expression of Syndecan 3 and Connexin 43 in Human Uterine Tissue," Reproduc. Biol. Endocrinol. 4:24 (2006).
Ekman-Ordeberg et al., "Low Molecular Weight Heparin Stimulates Myometrial Contractility and Cervical Remodeling In Vitro," Acta Obstetricia et Gynecologica 88:984-989 (2009).

(Continued)

*Primary Examiner* — Ganapathy Krishnan
(74) *Attorney, Agent, or Firm* — LeClairRyan, a Professional Corporation

(57) ABSTRACT

The present invention relates to a chemically modified heparin, with an antifactor II activity of less than 10 IU/mg, an antifactor Xa activity of less than 10 IU/mg and an average molecular weight (Mw) between about 6.5 and 9.5 kDa. Also disclosed is a method of preparing the heparin and its medical use, including treatment of malaria.

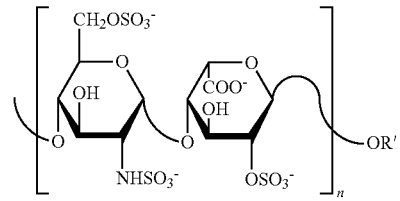

29 Claims, 8 Drawing Sheets

(56) References Cited

FOREIGN PATENT DOCUMENTS

| WO | 2009/073184 A1 | 6/2009 |
| WO | 2009124266 A2 | 10/2009 |
| WO | 2010/121196 A1 | 10/2010 |
| WO | 2011000032 A1 | 1/2011 |
| WO | 2013/095277 A1 | 6/2013 |
| WO | 2013/095279 A1 | 6/2013 |
| WO | 2013/147689 A1 | 10/2013 |
| WO | 2013/147690 A1 | 10/2013 |

OTHER PUBLICATIONS

Belghiti et al., "Oxytocin During Labour and Risk of Severe Postpartum Haemorrhage: A Population-Based, Cohort-Nested Case-Control Study," BMJ Open 1(e000514):1-9 (2011).

Su, "Postpartum Hemorrhage," Prim. Care Clin. Office Pract. 39:167-187 (2012).

Fransson et al., "Relationship Between Anticoagulant Activity of Heparin and Susceptibility to Periodate Oxidation," FEBS Lett. 97(1):119-123 (1979).

Vogt et al., "Release of Sequestered Malaria Parasites Upon Injection of a Glycosaminoglycan," PLOS Path. 2 (9):0853-0863 (2006).

Dondorp et al., "Levamisole Inhibits Sequestration of Infected Red Blood Cells in Patients with Falciparum Malaria," J. Infect. Dis. 196:460-466 (2007).

Silamut et al., "A Quantitative Analysis of the Microvascular Sequestration of Malaria Parasites in the Human Brain," Am. J. Pathol. 155(2):395-410 (1999).

Dilafor press release: Potential Treatment for Severe Malaria completes Phase I Study (Oct. 13, 2009).

Dilafor press release: Dilafor Announces the Selected INN for DF02, Sevuparin (Aug. 30, 2010).

Dilafor press release: Dilaforette Initiates a Phase I/II Study with Sevuparin for the Treatment of Severe Malaria (Sep. 23, 2011).

Who Drug Information, 25(4):437-438 (2011).

Who Drug Information, 26(3):323 (2012).

Lindahl et al., "Evidence for a 3-O-Sulfated D-Glucosamine Residue in the Antithrombin-Binding Sequence of Heparin," Proc. Nat. Acad. Sci. U.S.A. 77(11):6551-6555 (1980).

Casu et al., "Undersulfated and Glycol-Split Heparins Endowed with Antiangiogenic Activity," J. Med. Chem. 47:838-848 (2004).

Naggi et al., "Glycol-Splitting as a Device for Modulating Inhibition of Growth Factors and Heparanase by Heparin and Heparin Derivatives," Chemistry and Biology of Heparin and Heparin Sulfate, Elsevier, Amsterdam pp. 461-481 (2005).

Naggi et al., "Modulation of the Heparanase-Inhibiting Activity of Heparin through Selective Desulfation, Graded N-Acetylation, and Glycol Splitting," J. Biol. Chem. 280(13):12103-12113 (2005).

Pisano et al., "Undersulfated, Low-Molecular-Weight Glycol-Split Heparin as an Antiangiogenic VEGF Antagonist," Glycobiol. 15(2):1C-6C (2005).

Alekseeva et al., "Profiling Glycol-Split Heparins by HPLC/MS Analysis of their Heparinase-Generated Oligosaccharides," Anal. Biochem. 434(1):112-122 (2013).

Alekseeva et al., "Structural Features of Glycol-Split Low-Molecular-Weight Heparins and their Heparin Lyase Generated Fragments," Anal. Bioanal. Chem. 406:249-265 (2014).

Clinicaltrials.gov: A Phase I/II, Randomized, Open Label, Active Control, Parallel Assignment, Safety/Efficacy Study of Sevuparin/ DF02 as an Adjunctive Therapy in Subjects Affected with Uncomplicated Falciparum Malaria (May 7, 2015).

Carlson et al., "Disruption of Plasmodium Falciparum Erythrocyte Rosettes by Standard heparin and Heparin Devoid of Anticoagulant Activity," Am. J. Trop. Med. Hyg. 46(5):595-602 (1992).

von der Lehr, "Battle Against Clever Parasite," Kemisk Tidskrift Nr 7-8:24-26 (2011).

Kulane et al., "Effect of Different Fractions of Heparin on Plasmodium Falciparum Merozoite Invasion of Red Blood Cells In Vitro," Am. J. Trop. Med. Hyg. 46(5):589-594 (1992).

Ware et al., "Advances in the Use of Hydroxyurea," Am. Soc. Hematol. pp. 62-69 (2009).

Chaplin et al., "Preliminary Trial of Minidose Heparin Prophylaxis for Painful Sickle Cell Crises," E. African Med. J. 66 (9):574-584 (1989).

Qari et al., "Reduction of Painful Vaso-Occlusive Crisis of Sickle Cell Anaemia by Tinzaparin in a Double-Blind Randomized Trial," Thromb. Heamost. 98:392-396 (2007).

Blumenkrantz et al., "New Method for Quantitative Determination of Uronic Acids," Analytical Biochem. 54:484-489 (1973).

Bachelet et al., "Affinity of Low Molecular Weight Fucoidan for P-Selectin Triggers its Binding to Activated human Platelets," Biochimica Biophysica Acta 1790:141-146 (2009).

Zennadi et al., "Epinephrine Acts Through Erythroid Signaling Pathways to Activate Sickle Cell Adhesion to Endothelium via LW-{alpha}v{beta}3 Interactions," Blood 104:3774-3781 (2004).

Zennadi et al., "Epinephrine-Induced Activation of LW-Mediated Sickle Cell Adhesion and Vaso-Occlusion In Vivo," Blood 110:2708-2717 (2007).

Batchvarova et al., "Sevuparin Reduces Adhesion of Both Sickle Red Cells and Leukocytes to Endothelial Cells In Vitro and Inhibits Vaso-Occlusion In Vivo," Abstract #58733, New Orleans 7-10 (Dec. 2013) (ASH).

Brodszki et al., "A Novel Treatment Approach for Paediatric Gorham-Stout Syndrome with Chylothorax," Acta Paediatrica 100:1448-1453 (2011).

Fransson et al., "Structural Studies on Heparan Sulphates. Characterization of Oligosaccharides; Obtained by Periodate Oxidation and Alkaline Elimination," Eur. J. Biochem. 106:59-69 (1980).

Guerrini et al., "Complex Glycosaminoglycans: Profiling Substitution Patterns by Two-Dimensional Nuclear Magnetic Resonance Spectroscopy," Analytical Biochem 337:35-47 (2005).

Shaker et al., "Uterine Contractions Due to Heparin," British Med. J. pp. 408-409 (1974).

Osmers et al., "Glycosaminoglycans in Cervical Connective Tissue During Pregnancy and Parturition," Obst. Gynecol. 81(1):88-92 (1993).

Blanks et al., "Myometrial Function in Prematurity," Best Pract. Res. Clin. Obst. Gynaecol. 21(5):807-819 (2007).

Combs et al., "Factors Associated With Hemorrhage in Cesarean Deliveries," Obstetrics and Gynecology, 77(1):77-82 (1991).

Henry et al., "Perinatal Outcomes in the Setting of Active Phase Arrest of Labor," Obstetrics and Gynecology,112(5): 1109-1115 (2008).

Isma et al., "The Effect of Low Molecular Weight Heparin (Dalteparin) on Duration and Initiation of Labour," J Thromb Thrombolysis 30:149-153 (2010).

The Merck Manual of Diagnosis and Therapy, 17th Ed., Beers and Berkow, Eds., Ch. 253. " Abnormalities and Complications of Labor and Delivery,"; Ch. 254: "Postpartum Care"; pp. 2062-2067 (1999).

Alfirevic et al.,"Prevention of Post-Partum Hemorrhage with Misoprostol," Int. J. Gynecology Obstetrics 99:S198-S201 (2007).

Dildy, "Postpartum Hemorrhage: New Management Options," Clinc. Obstetrics & Gynecology 45(2):330-344 (2002).

Rudd et al., "High-Sensitivity Visualization of Contaminants in Heparin Samples by Spectral Filtering of 'H NMR Spectra," Analyst 136:1390-1398 (2011).

Wei et al., "High-Dose vs Low-Dose Oxytocin for Labor Augmentation: A Systematic Review," Am. J. Obstetrics & Gynecology 203(4): 296-304 (2010).

Kadanali et al., "Comparison of Labor Induction with Misoprostol vs. Oxytocin/Prostaglandin E2 in Term Pregnancy," International Journal of Gynecology & Obstetrics 55:99-104 (1996).

Belayet et al., "Binding of Interleukin-8 to Heparan Sulphate Enhances Cervical Maturation in Rabbits," Molecular Human Reproduction 5(3):261-269 (1999).

Ekman-Ordeberg et al., "Tafoxiparin a New Drug Counteracting Labor Arrest by Increased Myometiral Contractility and Enhanced Cervical Cytokine Synthesis," Poster Presented at Birth Labor Congress (Chicago, 2011) and Society of Gynecologic Investigations (Miami, 2010).

(56) References Cited

OTHER PUBLICATIONS

Dilafor press release: Promising Results from Phase II Trial Show New Treatment from Dilafor Prevents Protracted Labor in Childbirth (Sep. 3, 2009).

Barragan et al., "The Duffy-Binding-Like Domain 1 of Plasmodium falciparum Erythrocyte membrane Protein 1 (PfEMP1) is a Heparan Sulfate Ligand that Requires 12 Mers for Binding," Blood 95(11):3594-3599 (2000).

Ekman-Ordeberg et al., "Does Low Molecular Weight Heparin Shorten Term Labor?" Acta Obstetricia et Gynecologica 89:147-150 (2010).

Lau et al., "Inhibitors of Slit Protein Interactions with the Heparan Sulphate Proteoglycan Glypican-1: Potential Agents for the Treatment of Spinal Cord Injury," Clin. Exper. Pharmacol. Physiol. 37:417-421 (2010).

Skidmore et al., "Disruption of Rosetting in Plasmodium falciparum Malaria with Chemically Modified Heparin and Low Molecular Weight Derivatives Possessing Reduced Anticoagulant and Other Serine Protease Inhibition Activities," J. Med. Chem. 51:1453-1458 (2008).

Wiesner et al., "New Antimalarial Drugs," Angew. Chem. Int. Ed. 42:5274-5293 (2003).

Akerud, "Uterine Remodeling During Pregnancy. Studies on the Effect of Heparin/Heparan Sulfate," Department of Experimental Medical Science (2009).

WHO Drug Information 23(4) Proposed International Nonproprietary Names for Pharmaceutical Substances: List 102 (2009).

International Nonproprietary Names for Pharmaceutical Substances: List 64, p. 24.

Karolinska Development Press Release—Portfolio Company Completes Successful Phase II Clinical Trial (Sep. 4, 2009).

Invitation to Subscribe for Shares in Karolinska Development p. 45 (Mar. 25, 2011) p. 46 (Apr. 14, 2011).

Clinicaltrials.gov: A Randomized, Double-Blind, Placebo-Controlled, Multicenter Trial to Assess the Safety and Efficacy or Pre-Treatment with DF01 During Later Pregnancy in Reducing Prolonged Labor (May 19, 2015).

Roos et al., "Prostaglandin Receptors in the Human Cervix at Term and Post Term Pregnancy—Genetic Expression and Localization," Poster S-071 Reproduct. Sci. 18(4):Supplement (Mar. 2011).

Van Lennep et. al., "Prophylaxis with Low-Dose Low-Molecular-Weight Heparin During Pregnancy and Postpartum: Is It Effective?," Journal of Thrombosis and Haemostasis, 9:473-480 (2011).

Yousuf and Haider, "Postpartum Hemorrhage: An Experience At Tertiary Care Hospital," 14(2):80-84 (2009).

Bazin et al., "Inhibition of Apolipoprotein E-Related Neurotoxicity by Glycosaminoglycans and Their Oligosaccharides," Biochemistry 41(25):8203-8211 (2002).

Garg et al., "Heparin Oligosaccharide Sequence and Size Essential for Inhibition of Pulmonary Artery Smooth Muscle Cell Proliferation," Carbohydrate Research 337(21-23):2359-2364 (2002).

Guerinni et al., "Antithrombin-binding Octasaccharides and Role of Extensions of the Active Pentasaccharide Sequence in the Specificity and Strength of Interaction: Evidence for Very High Affinity Induced by an Unusual Glucuronic Acid Residue," J. of Biol. Chem 283(39):26662-26675 (2008).

Leitgeib et al., "Low Anticoagulant Heparin Disrupts Plasmodium falciparum Rosettes in Fresh Clinical Isolates," Am J. Trop. Med. Hyg. 84(3):390-396 (2011).

Suda et al. "Structural Characterization of Heparin's Binding Domain for Human Platelets," Thrombosis Research 69 (6):501-508 (1993).

International Search Report for PCT/SE2011/051538 (mailed Sep. 3, 2012).

International Search Report and Written Opinion for PCT/SE2012/051428 (mailed Apr. 17, 2013).

* cited by examiner

GlcN - UA - GlcN - UA - GlcN - UA - GlcN

R= –H or –SO$_3^-$

R'= COCH$_3$ or –SO$_3^-$

R= COCH$_3$ or –SO$_3^-$

LOW ANTICOAGULANT HEPARINS

TECHNICAL FIELD

The present invention relates to chemically modified heparins with low anticoagulant activity and methods of its production. The chemically modified heparins are useful for treating disorders where heparin has been regarded as effective, but considered too prone to side effects, such as malaria.

BACKGROUND OF THE INVENTION

Heparin is a naturally occurring GAG (glucosaminoglycan) that is synthesized by and stored intracellulary in so-called mast cells in humans and animals. Prepared industrially from porcine intestinal mucosa, heparin is a potent anticoagulant and has been used clinically for more than 60 years as the drug of preference for prophylaxis and treatment of thromboembolic disorders. The major potential adverse effects of heparin treatment are bleeding complications caused by its anticoagulant properties. Heparin is highly polydisperse and composed of a heterogeneous population of polysaccharides with molecular weights ranging from 5 to 40 kDa, with the average being approximately 15 to 18 kDa. Low molecular weight/mass heparins (LMWH) according to European pharmacopeia 6.0 are defined as "salts of sulfated GAGs having a mass-average molecular mass less than 8 and for which at least 60 per cent of the total mass has a molecular mass less than 8 kDa." Low molecular mass heparins display different chemical structures at the reducing or the non-reducing end of the polysaccharide chains." "The potency is not less than 70 IU of anti-factor Xa activity per milligram calculated with reference to the dried substance. The ratio of anti-factor Xa activity to anti-factor IIa activity is not less than 1.5." Clinically used LMWHs have molecular weights ranging from 3 to 15 kDa with an average of approximately 4 to 7 kDa. Produced by controlled depolymerization/fractionation of heparin, LMWHs exhibits more favorable pharmacological and pharmacokinetic properties, including a lower tendency to induce hemorrhage, increased bioavailability and a prolonged half-life following subcutaneous injection.

Heparin exerts its anticoagulant activity primarily through high-affinity binding to and activation of the serine proteinase inhibitor, antithrombin (AT). Binding is mediated by a specific pentasaccharide sequence. AT, an important physiological inhibitor of blood coagulation, neutralizes activated coagulation factors by forming a stable complex with these factors. Binding of heparin causes a conformational change in AT that dramatically enhances the rate of inhibition of coagulation factors, thereby attenuating blood coagulation and the formation of blood clots.

Infection caused by *Plasmodium falciparum* frequently gives rise to severe malaria in humans. Parasitized erythrocytes (pE) have the ability to bind (in vivo: sequestrate) in the deep microvasculature as well as to uninfected erythrocytes, so called rosetting. The sequestration and rosetting of pE augments the generation of severe disease when binding is excessive; blocking the blood-flow, reducing oxygen delivery and causing tissue damage. Heparin has been suggested as a useful agent in the treatment of the pathology occurring during severe malaria. Heparin was previously used in the treatment of severe malaria because of the suggested presence of disseminated intravascular coagulation (DIC) in malaria patients but it was discontinued due to the occurrence of severe side effects such as intracranial bleedings. Moreover, it was found that pE aggregation is not primarily due to blood coagulation, but to noncovalent interactions between a parasite-induced protein on pE surfaces and heparan sulfate (a heparin-related GAG) on erythrocytes and vascular endothelial cells. The effect of heparin is ascribed to its ability to compete out this interaction (Vogt et al., PloS Pathog. 2006; 2, e100). Hence, there is a medical need for a heparin derivative with a markedly reduced anticoagulant activity and bleeding inducing potential designed with respect to its distribution of suitable sized and charged chains. U.S. Pat. No. 5,472,953 (Ekre et al) discloses the use of heparins with reduced anticoagulant activity for the treatment of malaria.

A M Leitgeib et al. in Am. J. Trop. Med. Hyg. 2011, vol. 84(3), pp. 380-396 report promising studies with low anticoagulant heparins which are found to disrupt rosettes of fresh clinical isolates from patients with malaria.

In summary, a heparin derivative that carries the polyanionic features of heparin in essential respects, but lacks an anticoagulant effect would be an excellent candidate for treating maladies in which the anticoagulant effect of heparin would be considered as a serious side effect.

DESCRIPTION OF THE INVENTION

The present invention relates to chemically modified heparins that is selectively prepared to retain therapeutic effects from the polysaccharide chains, while having a low anticoagulant effect.

In the context of the present invention, anti-coagulant activity of heparin relates to the clinical function of potentiating inhibition of coagulation factors Xa and IIa (thrombin) by AT. Other terms will be defined in relevant contexts in the following description.

In one aspect, the invention relates to a method of preparing chemically modified heparin with an antifactor II activity of less than 10 IU/mg, an antifactor Xa activity of less than 10 IU/mg and an average molecular weight (weight average, Mw) from about 6.5 to about 9.5 kDa. The method generally comprises a step of selectively oxidizing heparin present in an aqueous solution by subjecting it to an oxidizing agent capable of oxidizing non-sulfated saccharide residues and followed by reducing the resulting oxidized saccharide residues. The method also generally comprises depolymerizing the oxidized and reduced heparin chains by hydrolysis at an acid pH from about 3 to about 4. The method can be performed in the general sequence, consecutively by oxidizing, reducing and depolymerizing with hydrolysis in the manners just described, while other complementary process steps may be added in any suitable order.

The depolymerization is performed at a temperature of at least about 20° C. in order to obtain suitably fractioned chains with desirable molecular weights. In order to support selection of desirable chains, the method generally can also include a step of enriching polysaccharide chains having a molecular weight of about from 5.5 to about 10.5 kDa. The enrichment step generally includes conventional chromatographic, filtering or sieving procedures well known to those skilled in biopolymer manufacturing.

The methods according to the invention can further comprise at least one step of eliminating remaining oxidizing agent.

In addition, the methods according to the invention may comprise at least one elimination step which includes removing reduced forms of the oxidation agent. In this context reduced forms means oxidation agent transformed to reduced forms from contributing to oxidation of targeted saccharide residues in heparin. Also in this context, the reduction step can comprise addition of a reducing agent which apart from reducing the oxidized heparin, contribute to consumption (reducing) of remaining oxidizing agent.

In one aspect, the method according to the invention comprises a step of eliminating any remaining oxidizing agent and removing reduced forms of oxidizing agent between the described reducing step and the described depolymerization step. The depoylmerization can be performed with hydrolysis at pH from to 3.0 to 3.5.

Accordingly, in one aspect, the invention is directed to a method comprising the consecutive steps of selectively oxidizing an unfractionated heparin by subjecting it to an oxidizing agent capable of oxidizing non-sulfated saccharides; reducing the resulting oxidized saccharides; eliminating remaining oxidizing agent and reduced forms of oxidizing agent; and depolymerizing the heparin chains by hydrolysis at an acidic pH from about 3 to about 3.5.

The elimination step may comprise adding an alcohol in an amount sufficient for the chemically modified heparin to precipitate. The alcohol can be methanol, ethanol or similar alcohols and admits the chemically modified heparin to precipitate, while the oxidizing agent and its reduced forms are removed with the alcohol.

The elimination step can also include addition of a quenching agent capable of chemically inactivating the oxidizing agent to further exert oxidizing effects on the heparin. It is generally considered by the inventors that the so described elimination step or elimination steps would contribute to counteract or minimize non-specific depolymerization of heparin, i.e. depolymerization effects not attributable to the predictable results of the acidic hydrolysis. Non-specific depolymerization may result in unpredictable loss in molecular weight, discolored products (with unstable absorbance values), other problems with stability and the appearance of unidentified residues not predicted to arrive in heparin or low molecular weight heparins.

The introduction of an elimination step after the oxidation step enables an improved control over any non-specific depolymerization. Another way of controlling non-specific depolymerization, applicable with any earlier described method, is to reduce the temperature significantly below ambient (room) temperature during the previous precipitation step or steps when adding an alcohol. For example, the temperature can be reduced to about 5° C. in order to prevent unwanted reactions resulting in non-specific depolymerization.

In accordance with the present invention, heparin is selectively oxidized, thereby inhibiting the anticoagulant effect mediated by the interaction between AT and the specific pentasaccharide. The oxidation selectively splits glycols with 2 adjacent free hydroxyls and the resulting product is referred to as a "glycol split" product. For this purpose the composition of unfractionated heparin is treated with a periodate compound, such as sodium metaperiodate in a suitable reaction medium, for example following the disclosures in U.S. Pat. No. 4,990,502. Other oxidation agents would be useful if they have the same chemical impact on the non-sulfated residues, without damaging critical levels of sulfates as required in the final product. When a periodate compound is used as an oxidizing agent, it is reduced to iodate and subsequently, in the reducing step, to other inert forms of iodine, collectively referred to as "iodine compounds". The elimination step of the inventive processes serves to eliminate or minimize the oxidative effect of any iodine compounds and to remove the iodine compounds from the process in a way that counteracts of minimizes non-specific depolymerization. For this reason, the elimination step can comprise one or two precipitation steps with alcohol. It can also include addition of a quenching agent with two vicinal hydroxyl groups, such as ethylene glycol, glycerol and similar agents, in order to chemically and selectively eliminate oxidizing agents.

The oxidized heparin, for example after isolation through alcohol precipitation, subsequently is treated with a reducing agent, suitably sodium borohydride, for example according to the protocols of U.S. Pat. No. 4,990,502. Other reducing agents may be used if they are capable of performing similar reduction of oxidized glucuronic/iduronic acid residues as sodium borohydride without unnecessarily modifying or destroying the sulfate groups of other saccharide residues. The so reduced chains can be isolated, for example by alcohol precipitation and transferred to the depolymerisation step.

The employment of unfractionated heparin in the so described methods is regarded as generally advantageous for the invention, since it will contribute towards reducing waste of material and increasing cost efficacy and support the provision of a composition product with desirable polysaccharide chain length and with retained sulfate groups The depolymerization step can be performed in an aqueous solution at a concentration from about 15 to about 25% w/v of the modified heparin. A strong acidifier is then admixed to the solution to a pH of from about 3 to about 4. A suitable pH range is from about 3.0 to about 3.5. A pH value of about 3.0 is suitable according to the inventive method, while pH 3.5 also has been found suitable and admits production of a chemically modified heparin within the outlined molecular weight range. It has been found that the inventive process admits flexibility in this pH range that can be controlled by the process time of the hydrolysis step when operating within a time frame of 4 to 10 hours. Hydrochloric acid is a suitable acid with the inventive process, however other strong acids can be found useful if they do not substantially destroy sulfate groups. By applying the above specified conditions, a product with suitable chain lengths and storage stability is retrieved for subsequent work up to a pharmaceutically useful composition.

The methods yield an overall enrichment in sulfate groups within the polysaccharide chain length as non-sulfated iduronic/glucuronic acid is chemically modified and appears mainly as reducing end, remnant terminals. The methods accordingly involve conditions that retain sulfate groups and thus to retain the sulfated domains of native heparin. The methods also yield chains with an advantageous size distribution which supports a desirable therapeutic efficacy and is considered to improve the therapeutic index compared to other described low anticoagulant heparins. The invention does in general terms extend to chemically modified heparins prepared with the recited methods.

The invention is directed to chemically modified heparins with an antifactor II activity of less than 10 IU/mg, an antifactor Xa activity of less than 10 IU/mg and an average molecular weight (Mw) between about 6.5 and about 9.5 kDa which can be manufactured with the described methods. Chemically modified heparin according to the invention has polysaccharide chains which retain at least 90% of the sulfate groups. Chemically modified heparin according to the invention have a loss of sulfate groups of about one sulfate group per disaccharide unit of 100 disaccharide units, corresponding to a loss of sulfate groups of less than 1% of the total sulfate content, when assuming that heparin contains in average 2.4 sulfate groups per disaccharide unit and that there is one sulfate group per iduronic acid, I2S and 2 sulfate groups for the predominant glucosamine variant, GlcNS.

An aspect of the invention is a chemically modified heparin with an antifactor II activity of less than 10 IU/mg, an antifactor Xa activity of up to 10 IU/mg and an average molecular weight from about 6.5 to about 9.5 kDa, wherein the polysaccharide chains:

(i) retain at least 90%, of the sulfate groups of the corresponding native heparin;
(ii) comprise from 2 to 25 disaccharide units corresponding to molecular weights from 1.2 to 15 kDa;
(iii) have a reduction in chemically intact saccharide sequences providing an antithrombin mediated anticoagulant effect, when compared to the polysaccharide chains of native heparin; and
(iv) have a reduction in unsulfated iduronic and/or glucuronic acid units when compared to native heparin.

A chemically modified heparin has from 2 to 25 disaccharide units corresponding to molecular weights from about 1.2 to about 15 kDa. A chemically modified heparin has polysaccharide chains with a reduction in chemically intact pentasaccharide sequences responsible for the antithrombin (AT) mediated anticoagulant effect, when compared to the chains of native heparin and have polysaccharide chains with a reduction in unsulfated iduronic and glucuronic acid residues when compared to native heparin.

An aspect of the invention is that chemically modified heparin having predominantly occurring polysaccharide chains with between 6 and 16 disaccharide units with molecular weights between 3.6 and 9.6 kDa. The term "predominantly" does in this context have the meaning of "the frequently most present" polysaccharide chains.

An aspect of the invention is a chemically modified heparin having at least 30% of the polysaccharide chains with a molecular weight of at least 8 kDa.

An aspect of the invention is a chemically modified heparins comprising chains terminated by a threonate residue or by a derivative of threonate, such as esters or amides thereof. The threonate residue is depicted below as a terminal group.

In an aspect of the invention, from 3 to 15% of the polysaccharide chains of the chemically modified heparin have a molecular mass of at least 15 kDa.

In an aspect of the invention, from 25 to 47% of the polysaccharide chains of the chemically modified heparin have a molecular mass of at least 9 kDa.

In an aspect of the invention, from 40 to 60% of the polysaccharide chains of the chemically modified heparin have a molecular mass of at least 7 kDa.

In an aspect of the invention, from 60 to 80% of the polysaccharide chains of the chemically modified heparin have a molecular mass of at least 5 kDa.

In an aspect of the invention, 85% of the polysaccharide chains of the chemically modified heparin have a molecular mass of at least 3 kDa.

In an aspect of the invention, 95% of the polysaccharide chains of the chemically modified heparin have a molecular mass of at least 2 kDa.

In yet an aspect, chemically modified heparin of the invention have a distribution of polysaccharides and their corresponding molecular mass expressed as cumulative % of weight according the table:

| Molecular mass, kDa | Cumulative weight, % |
|---|---|
| >15 | 3-15 |
| >9 | 25-47 |
| >7 | 40-60 |
| >5 | 60-80 |
| >3 | >85 |
| >2 | >95 |

In yet an aspect, chemically modified heparin of the invention have a distribution of polysaccharides and their corresponding molecular mass expressed as cumulative % of weight according the table:

| Molecular mass, kDa | Cumulative weight, % |
|---|---|
| >15 | 3-15 |
| >10 | 18-38 |
| >9 | 25-47 |
| >8 | 30-55 |
| >7 | 40-60 |
| >6 | 50-72 |
| >5 | 60-80 |
| >4 | 72-86 |
| >3 | >85 |
| >2 | >95 |

Chemically modified heparin according to the invention has polysaccharide chains with the disaccharide depicted below as the predominant structure with a terminal threonate residue. The predominant disaccharide has a molecular weight of about 600 Da.
(n is an integer of 2-25).

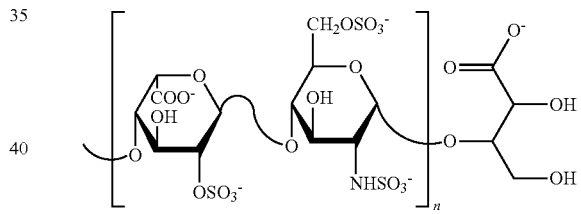

According to yet an aspect of the invention, chemically modified heparin according to the invention comprises glycol-split residues with the chemical structure:

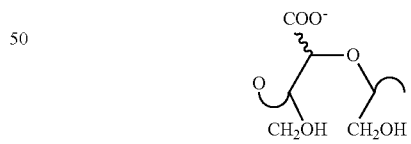

Glycol-split residues appear in polysaccharide chains of chemically modified heparins, as a result of the oxidation and reduction processes, as earlier discussed in the context with the method and the specific hydrolysis step. They can also be regarded as indicative of the efficacy of the earlier described depolymerization (hydrolysis) step. It is further referred to U.S. Pat. No. 4,990,502 for a chemical reference of the appearance of glycol-split residues. The depicted glycol-spilt residue arrives from oxidation and reduction of unsulfated iduronic acid and glucuronic acid.

Chemically modified heparin according to the invention has a $^1$H-NMR spectrum in the range of from 5.0 to 6.5 ppm that complies with a $^1$H-NMR spectrum from native heparin by the absence of any proton signals with a magnitude above 0.1 (mol) %.

In one aspect of the invention, chemically modified heparin as herein described complies with presently accepted heparin standards by having an $^1$H-NMR spectrum meeting the heparin acceptance criterion set out by EDQM, Council of Europe, 2012, for example by not having any unidentified signals larger than 4 percent compared to the height of the heparin signal at 5.42 ppm in the ranges 0.10-2.00 ppm, 2.10-3.10 ppm and 5.70-8.00 ppm.

In one aspect, chemically modified heparin according to the invention has a relative average molecular mass range of approximately 7,500 daltons with about 90% ranging between 2,000 and 15,000 daltons; the degree of sulfation is 2 to 2.5 perdisaccharidic unit.

In one aspect of the invention, a chemically modified heparin as herein described, may be useful for therapies previously disclosed as associated with other regions of heparin than the binding site to AT. Examples include, but are not limited, to such areas as treatment of inflammation, treatment of neurodegenerative diseases, tissue repair, stroke, prevention and treatment of shock, especially septic shock and prevention of the development of metastases.

An aspect of the invention, is a chemically modified heparin for use in the treatment of malaria. Chemically modified heparins as herein disclosed, may be useful in the preventionor treatment of occlusive effects from malaria, caused by abnormal adhesive effects in the blood.

An aspect of the invention is a combination of chemically modified heparin as herein disclosed, with another malaria medicament. In one aspect of the invention, such combinations comprise chemically modified heparin and atovaquone/proguanil or artesunate (parenteral). Examples of malaria medicaments in combination aspects of the inventions medicaments are, for use alone, or combinations with each other, are artemether, lumefantrine, amodiaquine, mefloquine, sulfadoxine, pyrimethamine, tetracycline, doxycycline, dapsone, clindamycin, quinine, tetracycline, atovaquone, proguanil, chloroquine, primaquine, sulfadoxin, amodiaquine, dihydroartemisini, piperaquine, dihydroartemisinin, and piperaquine In still an aspect of the invention, a chemically modified heparin as herein disclosed may be administered simultaneously or sequentially with a malaria medicament, i.e. in an adjunct therapy with a malaria medicament.

The term "malaria medicament" includes agents conventionally used for treating malaria, such as agents already established for treating the parasite infection. Yet an aspect of the invention, is a method for the treatment of malaria, comprising the administration to patient in need of such treatment, a therapeutically effective amount of a chemically modified heparin as herein described.

Yet an aspect of the invention is a pharmaceutical composition comprising a chemically modified heparin as herein described, together with a pharmaceutically and pharmacologically acceptable carrier. In yet an aspect of the invention, a pharmaceutical composition as herein described, may be administered systemically by parenteral administration, such as by subcutaneous or intravenous injection. In yet an aspect, a pharmaceutical composition as herein described, may be administered orally. For parenteral administration, the active compounds can be incorporated into a solution or suspension, which also contain one or more adjuvants such as sterile diluents such as water for injection, saline, fixed oils, polyethylene glycol, glycerol, propylene glycol or other synthetic solvents, antibacterial agents, antioxidants, chelating agents, buffers and agents for adjusting the osmolality. The parenteral preparation can be delivered in ampoules, vials, prefilled or disposable syringes also for self administration, or as infusion arrangements, such as for intravenous or subcutaneous infusion. Chemically modified heparins according to the invention may be administered subcutaneously and with suitable self-administration tools, such as injectors.

Pharmaceutical compositions comprising a chemically modified heparin as herein described, can comprise combinations of one or several conventional pharmaceutically acceptable carriers. The carriers or excipients can be a solid, semisolid or liquid material that can serve as a vehicle for the active substance. The compositions can be administered in a single dose every 24 h for a period of 1-30, preferably 1-10 days. The dose may be between 0.5-6 mg/kg bodyweight given, either intravenously every 6 or 8 hours, or 1-4 times daily given subcutaneously. An estimated single dose is 25-100 mg/d of a chemically modified heparin, but may be up to 1 g or more. The dose is related to the form of administration. The described pharmaceutical compositions can further comprise additional agents suitable for treating malaria with supplementary or complementary therapies as outlined in the previous section. A chemically modified heparin of the invention would need to retain a sufficient amount of the sulfate groups included in the native form, in order to exert a therapeutic activity unrelated to anticoagulant effects, for example by targeting *P. falciparum* erythrocyte membrane protein 1 (PfEMP1), and, at the same time have the anticoagulant activity inherent in the pentasaccharide abolished or largely reduced. Also, the inventors understand that selectin inhibition, as well as other heparin-dependent biological effects, correlate to polysaccharide chain length, so the chemical modification cannot result in extensive fragmentation of the native molecules. The bioavailability of long-chain heparins after subcutaneous dosing is low and the possibility of heparin induced thrombocytopenia (HIT) is positively correlated to chain length, the chemically modified heparin derivatives according to the invention should not be of full length. The present chemically modified heparin is the result of a number of important considerations 1. Initially, in order to satisfy the process economy criteria, the target heparin had to be able to be produced from unfractionated heparin. 2. The process can not yield too abundant short chains as the therapeutic effect is positively correlated with sufficiently long saccharide chain lengths. 3. The process should not yield too abundant long chains as the desirable subcutaneous dosing regime is not possible with longer chains. 4. Similarly, long chain length is correlated with undesirable side-effects such as HIT. 5. The process should eliminate the anticoagulant effect inherent in the AT-binding pentasaccharide. 6. The process shall avoid desulfatation of the polymer, but should rather increase the proportion of the sulfated residues, as therapeutic effects are positively correlated with the degree of sulfatation, that provides negative charge density. The invention as described above and to be described in the following detailed experimental section demonstrates that it is possible to overcome the hurdles that are outlined above and thus to produce a successful drug candidate, for treating malaria.

Detailed and Exemplifying Description of the Invention

One aspect of the invention is chemically modified heparins having the International proprietary name (INN) sevuparin sodium also given the code DF02. These terms are used interchangeably and shall have same meaning.

DESCRIPTION OF THE DRAWINGS

FIG. 2 shows the structure of the pentasaccharide unit in heparin required for its binding to AT.

EXAMPLE 1

Figure 1:
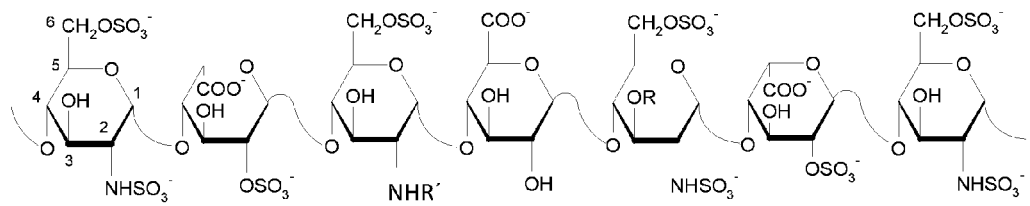
FIG. 1 shows a representative example of heparin sequence
Figure 2:
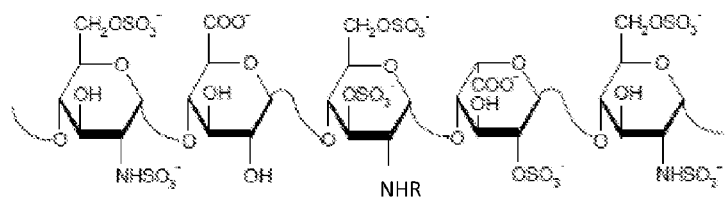
Figure 3:
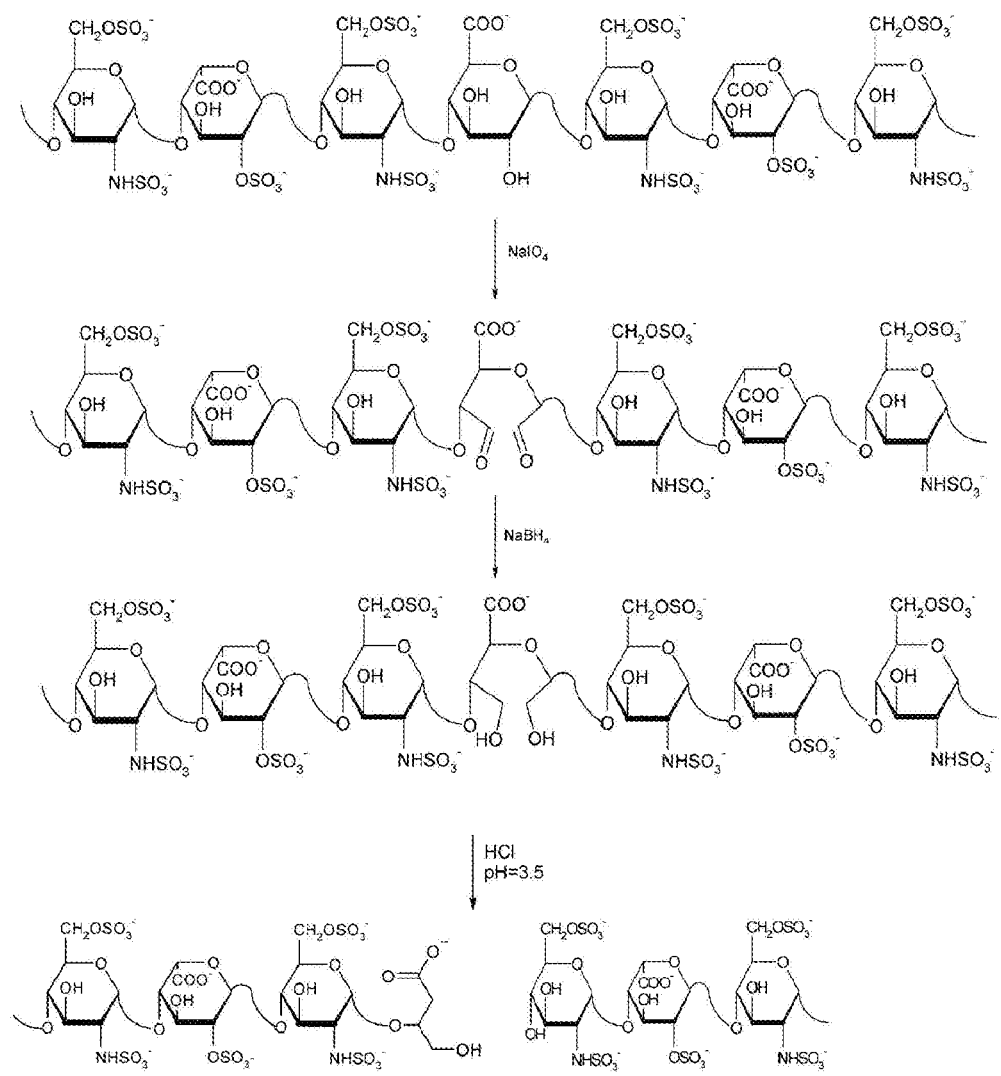
FIG. 3 shows a scheme of the synthesis of the chemically modified heparin DF02.
Figure 4:
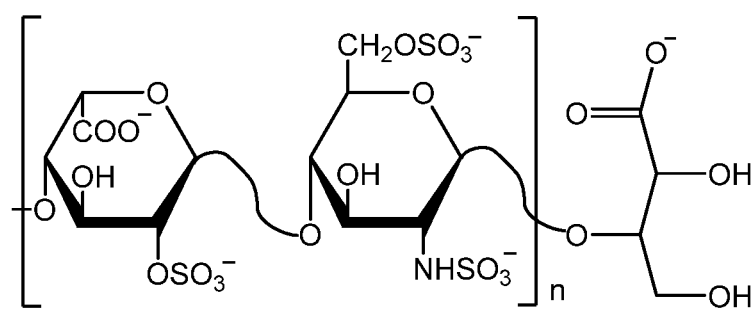
FIG. 4 shows the predominant structure of DF02.

Both heparin and LMWH are composed of repeating disaccharide units containing one uronic acid residue (D-glucuronic or L-iduronic acid, UA) and one D-glucosamine moiety (GlcN) that is either N-sulfated or N-acetylated. These carbohydrate residues may be further O-sulfated, at the C-6 and C-3 positions in the case of glucosamine and the C-2 position of the UA. The structure of heparin is variable regarding distribution of UA and sulfate residues; a representative partial sequence is shown in FIG. 1 (which also illustrates the mode of numbering of carbon atoms in a monosaccharide residue). FIG. 2 shows the unique, pentasaccharide sequence distributed within heparin polymers which is essential for the binding to AT. Several structural characteristics of this sequence have been shown to be crucial for the interaction of heparin with AT. Notably, one of the two UA residues present in this pentasaccharide sequence is consistently sulfated at the C-2 position; whereas the hydroxyl groups at both C-2 and C-3 of the other uronic moiety are unsubstituted Detailed Description of the Manufacturing Process of Chemically Modified Heparins According to the Invention FIG. 3 schematically shows the manufacturing of a chemically modified heparin according to the present invention, hereinafter designated DF02, while the following sections outline the manufacturing steps.

The substance is prepared from Heparin Sodium. The preparation involves selective oxidation of non-sulfated ironic acid residues in heparin by period ate, including the glucuronic acid moiety in the pentasaccharide sequence that binds AT. Disruption of the structure of this residue annihilates the high-affinity interaction with AT and, consequently, the anticoagulant effect (measured as a-FXa or a-FIIa, see Table 4 and 5). Subsequent reduction and treatment by acid results in cleavage of the polymer at the sites that has been oxidized by periodate. Together, these manipulations lead to a loss of anticoagulant activity along with adequate depolymerization of the heparin chain.

Subsequently, additives, impurities and side-products are removed by repeated precipitations with ethanol, filtration and centrifugations. Thereafter the substance is obtained in powder form by drying with vacuum and heat. The drug substance DF02 is dissolved in a sterile aqueous buffer to yield the drug product, which is intended for intravenous or subcutaneous administration.

Oxidation of Glucuronic and Iduronic Acid (Residues), Deletion of Anticoagulant Activity A quantity of about 3000 grams of Heparin is dissolved in purified water to obtain a 10-20% w/v solution. The pH of this solution is adjusted to 4.5-5.5. The sodium metaperiodate ($NaIO_4$) is subsequently added to the process solution, quantity of periodate 15-25% of the weight of heparin. The pH is again adjusted to 4.5-5.5. The reactor is covered in order to protect the reaction from light. The process solution is reacted during 22-26 hours with constant stirring and maintenance of the temperature at 13-17° C. The pH at the end of the reaction period is measured and recorded.

Termination of the Oxidation Reaction and Removal of Iodine-Containing Compounds Ethanol (95-99.5%) is added to the reaction mixture over a period of 0.5-1 hour, with careful stirring and at a temperature of 20-25° C. The volume of ethanol to be added is in the range 1-2 volumes of ethanol per volume of process solution. The oxidized heparin is then allowed to precipitate and sediment for 15-20 hours, after which the mother liquor is decanted and discarded.

Next, the sediment is dissolved in purified water to obtain a 15-30% w/v process solution. Then NaCl is added to obtain a concentration of 0.15-0.30 mol/liter in the process solution. Stirring continues for another 0.5-1 hour while maintaining the temperature of 20-25° C. Subsequently 1.0-2.0 volumes of ethanol (95-99.5%) per volume of process solution is added to this solution with careful stirring, during a period of 0.5-1 hour. This precipitates the product from the solution. This precipitation continues for >1 hour.

Reduction of Oxidized Glucuronic/Iduronic Acids

After the mother liquor has been decanted and discarded, the sediment is dissolved by addition of purified water until a concentration of the process solution of 15-30% w/v is obtained. While maintaining the temperature at 13-17° C., the pH of the solution is adjusted to 5.5-6.5. A quantity of 130-150 grams of sodium borohydride is then added to the solution and dissolved, the pH will immediately increase to a pH of 10-11, and the reaction is continued for 14-20 hours. The pH of the solution, both prior to and after this reaction period, is recorded. After this reaction time, a dilute acid is added slowly in order to adjust the pH to a value of 4, this degrades remaining sodium borohydride. After maintaining a pH of 4 for 45-60 minutes, the pH of the solution is adjusted to 7 with a dilute NaOH solution.

Acid Hydrolysis to Achieve Depolymerization of the Polysaccharide Chains

A dilute acid is added to the solution until a pH of 3.5 (acceptable range 3.2-3.8) is obtained. The temperature is kept at 50-55° C. while stirring the solution for 3 hours+/−10 minutes. A dilute NaOH solution is then added until a pH of 7.0 is obtained and the reaction solution is cooled down to a temperature of 13-17° C. Sodium chloride (NaCl) is then added until a concentration of 0.2-0.3 mol/liter is obtained.

Purification of the Product

Removal of Process Additives and Impurities, Addition of Counter-Ions and Filtration One volume of process solution is then added to 1.5-2.5 volumes of ethanol (95-99.5%) followed by centrifugation at >2000 G, and at <20° C. for 20-30 minutes, after which the supernatant is decanted and discarded.

The product paste obtained by centrifugation is then dissolved in purified water to obtain a product concentration 10-20% w/v. Then NaCl is added to obtain a concentration of 0.20-0.35 mol/liter. Further, 1.5-2.5 volumes of ethanol (95-99.5%) is added per volume of process solution which precipitates the product from the solution. Centrifugation follows at >2000 G, and at <20° C. for 20-30 minutes after which the supernatant is decanted and discarded. Next the remaining paste is added purified water to dissolve. The product concentration would now be in the range of 10-20% w/v. The pH of the product solution is now adjusted to 6.5-7.5. The solution is then filtered to remove any particulates. Then, to one volume of process solution is added 1.5-2.5 volumes of ethanol (95-99.5%). Centrifugation follows at >2000 G, and at <20° C. for 20-30 minutes after which the supernatant is decanted and discarded.

Reduction of the Size and Water Content of the Precipitate Paste

A glass reactor is then filled with ethanol, volume 2 liter. While stirring the ethanol, the precipitate paste is added. The mechanical stirring solidifies the paste and replaces the water present by the ethanol giving a homogenous particle suspension. The stirring is discontinued after 1-2 hours after which the particles are allowed to sediment, then the mother liquor is decanted. This procedure is repeated twice. The precipitate is isolated on a polypropylene (PP) filter. This procedure was repeated two more times. After removal of excessive liquid, the particles are passed through a sieve to obtain smaller and uniform sized particles.

Vacuum Drying

The product is distributed evenly onto two pre-weighed trays, and placed in a vacuum cabinet. The pressure is reduced with a vacuum pump, the pressure actually obtained being noted, and the trays are heated to 35-40° C., with constant recording of the temperature. A stream of nitrogen is passed through the drier at this time while maintaining the low pressure in the dryer. When a constant weight is obtained, i.e. no further evaporation is noticed, the drying is considered complete. The dry product is dispensed, packed and protected from moisture. Storage is performed in a dry area at a temperature of 20-25° C.

The so manufactured product can prepared as drug product by a conventional aseptic process, such as solution comprising 150 mg/mL of chemically modified heparin active agent and Na phosphate till 15 mM, pH 6-8. The so obtained drug product is intended for intravenous or subcutaneous administration. The resulting chemically modified heparin, DF02, is a depolymerized form of heparin with a projected average molecular weight of 6.5-9.5 kDa and with essentially no anticoagulant activity.

DF02 has a size distribution of polysaccharide polymers, with a range for n of 2-25 corresponding to molecular weights of 1.2-15 kDa. The predominant size is 6-16 disaccharide units corresponding to molecular weights of 3.6-9.6 kDa.

By practical tests it can be found that reaction of the oxidized heparin preparation in alkaline solution gives rise to chains that are too short, or lack the proper degree of sulfatation, for the optimal pharmaceutical function of the resulting heparin. Further by practical tests, it can be shown that treatment of the heparin preparation in a solution of less than pH 1, leads to desulfatation of the product, and thus giving rise to a chemically modified heparin with less than optimal pharmaceutical effect.

TABLE 1

Distribution of polysaccharides and their corresponding molecular mass in DF02 (several batches) as cumulative % of weight

| Molecular mass, kDa | Cumulative weight, % |
|---|---|
| >15 | 3-15 |
| >10 | 18-38 |
| >9 | 25-47 |
| >8 | 30-55 |
| >7 | 40-60 |
| >6 | 50-72 |
| >5 | 60-80 |
| >4 | 72-86 |
| >3 | >85 |
| >2 | >95 |

The corresponding value for weight average molecular weight, Mw falls in the range 6.5-9.5 kDa

TABLE 2

Distribution of polysaccharides and their corresponding molecular mass in DF02 as cumulative % of weight for an individual batch

| Molecular mass, kDa | Cumulative weight, % |
|---|---|
| >15 | 6.4 |
| >10 | 22.6 |
| >9 | 28.8 |
| >8 | 36.3 |
| >7 | 45.2 |
| >6 | 55.3 |
| >5 | 66.2 |
| >4 | 77.1 |
| >3 | 87.2 |
| >2 | 95.6 |

The corresponding value for molecular weight average weight, Mw is 7.4 kDa

EXAMPLE 2

Example 2 represents a modified version of the manufacturing process according to Example 1. Certain process parameters have been modified, such as process temperatures, with the purpose of preventing any non-specific depolymerization in the initial part of the process Oxidation of Glucuronic and Iduronic Acid (Residues), Deletion of Anticoagulant Activity A quantity of about 3000 grams of Heparin is dissolved in purified water to obtain a 10-20% w/v solution. The pH of this solution is adjusted to 4.5-5.5. The sodium metaperiodate ($NaIO_4$) is subsequently added to the process solution; quantity of periodate 15-25% of the weight of heparin. The pH is again adjusted to 4.5-5.5. The reactor is covered in order to protect the reaction from light. The process solution is reacted during the 22-26 hours with constant stirring and maintenance of the temperature at 13-17° C., while the temperature is lowered to about 5° C. during the last two hours. The pH at the end of the reaction period is measured and recorded.

Termination of the Oxidation Reaction and Removal of Iodine-Containing Compounds Ethanol (95-99.5%) is added to the reaction mixture over a period of 0.5-1 hour, with careful stirring and at a temperature of about 5° C. The volume of ethanol to be added is in the range 1-2 volumes of ethanol per volume of process solution. The oxidized heparin is then allowed to precipitate and sediment for 15-20 hours, after which the mother liquor is decanted and discarded.

Next, the sediment is dissolved in purified water to obtain a 15-30% w/v process solution. Then NaCl is added to obtain a concentration of 0.15-0.30 mol/liter in the process solution. Stirring continues for another 0.5-1 hour while maintaining a temperature of about 5° C. Subsequently 1.0-2.0 volumes of ethanol (95-99.5%) per volume of process solution is added to this solution with careful stirring, during a period of 0.5-1 hour. This precipitates the product from the solution. This precipitation continues for >1 hour.

Reduction of Oxidized Glucuronic/Iduronic Acids

This step is made in accordance with Example 1.

Acid Hydrolysis to Achieve Depolymerization of the Polysaccharide Chains

This step is performed in accordance with Example 1 with the difference that the process time may be extended about two hours before pH is raised to 7.0 with NaOH.

The further process steps towards a drug product comprising for example 150 mg/ml chemically modified heparin active agent is identical to the steps outline in Example 1.

By performing the process steps according to Example 2, a chemically modified heparin with a polysaccharide molecular weight distribution demonstrated in Table 1 of Example 1 is obtained.

EXAMPLE 3

Example 3 represents another method to manufacture chemically modified heparins according to the invention modified by directly subjecting the process solution arriving from the oxidation step to a strong reducing agent, before any precipitation step is introduced.

Oxidation of Glucuronic and Iduronic Acid (Residues), Deletion of Anticoagulant Activity A quantity of about 3000 grams of Heparin is dissolved in purified water to obtain a 10-20% w/v solution. The pH of this solution is adjusted to 4.5-5.5. The sodium metaperiodate ($NaIO_4$) is subsequently added to the process solution; quantity of periodate 15-25% of the weight of heparin. The pH is again adjusted to 4.5-5.5. The reactor is covered in order to protect the reaction from light. The process solution is reacted during the 22-26 hours with constant stirring and maintenance of the temperature at 13-17° C. The pH at the end of the reaction period is measured and recorded.

Reduction of Oxidized Glucoronic/Iduronic Acids and Elimination of Oxidizing Iodine Containing Compounds While maintaining the temperature at 13-17° C., the pH of the solution is adjusted to 5.5-6.5. A quantity of 130-200 grams of sodium borohydride is then added to the solution and dissolved, the pH will immediately increase to a pH of 10-11, and the reaction is continued for 14-20 hours. The pH of the solution, both prior to and after this reaction period, is recorded. After this reaction time, a dilute acid is added slowly in order to adjust the pH to a value of 4, this degrades remaining sodium borohydride. After maintaining a pH of 4 for 45-60 minutes, the pH of the solution is adjusted to 7 with a dilute NaOH solution.

Removal of Iodine-Containing Compounds

Ethanol (95-99.5%) is added to the reaction mixture over a period of 0.5-1 hour, with careful stirring and at a temperature of 20-25° C. The volume of ethanol to be added is in the range 1-2 volumes of ethanol per volume of process solution. The oxidized and subsequently reduced heparin is then allowed to precipitate and sediment for 15-20 hours, after which the mother liquor is decanted and discarded.

Next, the sediment is dissolved in purified water to obtain a 15-30% w/v process solution. Then NaCl is added to obtain a concentration of 0.15-0.30 mol/liter in the process solution. Stirring continues for another 0.5-1 hour while maintaining the temperature of 15-25° C. Subsequently 1.0-2.0 volumes of ethanol (95-99.5%) per volume of process solution is added to this solution with careful stirring, during a period of 0.5-1 hour. This precipitates the product from the solution. This precipitation continues for >1 hour.

Acid Hydrolysis to Achieve Depolymerization of the Polysaccharide Chains

After the mother liquor has been decanted and discarded, the sediment is dissolved by addition of purified water until a concentration of the process solution of 15-30% w/v is obtained.

A dilute acid is added to the solution until a pH of 3.0 is obtained. The temperature is kept at 50-55° C. while stirring the solution for 5 to 10 hours. The progress of depolymerization may be followed by in-process analyses of the molecular weight, by GPC-HPLC as to determine the actual time of reaction required. A dilute NaOH solution is then added until a pH of 7.0 is obtained and the reaction solution is cooled down to a temperature of 13-17° C. Sodium chloride NaCl is then added until a concentration of 0.2-0.3 mol/liter is obtained. Alternatively, in order to similarly control the average molecular weight, the dilute acid can be added to obtain a pH of 3.5, but to accomplish a comparable level of hydrolysis the process time is extended from 5 to 6 hour to 8 to 9 hours. According to both alternatives, the average molecular weight is kept well within the specification range of 6.5 and 9.5 kDa.

The remaining process steps towards a drug product comprising for example 150 mg/ml chemically modified heparin active agent is identical to the steps outline in Example 1.

By performing the process steps according to Example 3, a chemically modified heparin with a polysaccharide molecular weight distribution demonstrated in Table 1 of Example 1 is obtained.

TABLE 3

Intensity of signals present in $^1$H-NMR spectra compared to heparin in the range of 5 to 6.5 ppm

| Batch produced according to: | Intensity of signals % | | | |
|---|---|---|---|---|
| | 6.14 ppm | 6.00 ppm | 5.94 ppm | 5.90 ppm |
| Example 1 | 1.0 | 1.0 | 6.0 | 1.0 |
| Example 2 | 5.1 | 1.7 | 0 | 2.3 |
| Example 3 batch 1 | 0 | 0 | 0 | 0 |
| Example 3 batch 2 | 0 | 0 | 0 | 0 |
| Example 3 batch 3 | 0 | 0 | 0 | 0 |
| Heparin | 0 | 0 | 0 | 0 |

Table 3 is a result of comparing studies of $^1$H-NMR spectra in the range of 5.0 to 6.5 ppm, of chemically modified heparins produced according to Examples 1 to 3.

Table 3 confirms that a chemically modified heparin as manufactured with the process according to Example 3 results in a $^1$H-NMR spectrum with absence of unexpected signals in the range 5.90 ppm to 6.14 ppm equivalent to that of heparin. These signals show a correlation to partially unsaturated, double bond structures containing glucose amines, which may undergo further chemical modifications and contribute to discoloration of the product.

In other terms, the process according to Example 3, does not result in unidentified residues or structures that are unexpected in the proton spectra from conventional heparins or low-molecular weight heparin.

In order to confirm that methods according to the invention contribute to retain a desired level of sulfated polysaccharide chains, tests was performed with a sulfate measuring electrode on samples of process liquid from the step of acidic hydrolysis, i.e. samples from process liquid not subjected to the directly subsequent steps of work-up and purification to a chemically modified heparin product. The results demonstrate levels of released (lost) sulfate from polysaccharides generally below 1500 ppm. In other terms the tests confirm that the inventive methods induce a loss of sulfate groups not exceeding one sulfate group per disaccharide unit of 100 disaccharide units. chemically modified heparins according to the invention contain one sulfate group per iduronic acid, I2S and 2 sulfate groups for the predominant glucosamine variant, GlcNS. Accordingly, the chemically modified heparins according to the invention retain at least 90% sulfate groups corresponding to heparin.

Chemically modified heparin produced in accordance with processes of Example 3 and worked up to a product exhibit a very low absorbance at 400 nm (10% solution). Absorbance values vary between 0.02 AU and 0.04 AU for a product when subjected to the process including the hydrolysis at pH 3.5 or 3.0 respectively. The low absorbance values confirm that effects from any non-specific depolymerization associated with discoloration from side reactions of Maillard type (measured as absorbance at 400 nm) are minimized and that suitable stability of the chemically modified heparin products according to the invention are expected.

EXAMPLE 4

Antihaemostatic and Anticoagulation Effects

Studies on effects on coagulation parameters and on bleeding of DF02 were performed in male, adult and juvenile, Sprague-Dawley rats. Heparin and a LMWH preparation (Fragmin) were also studied for comparison. Basic test procedures were as follows:

Fifteen minutes after i.v. dosing of test article the rats had a longitudinal incision made at the dorsal mid-section of the tail. The incision was 9 mm long and 1 mm deep and was standardized using a template device. Blood was blotted from the incision until bleeding stopped. The time during which visible bleeding could be observed was measured, for up to 25 minutes. The longer the bleeding time, the more pronounced the anti-coagulant effects of the administered agent.

Adult Rat

Forty minutes after dosing, the rats were sacrificed by full bleeding. Citrate stabilized plasma was prepared from the blood. Plasma was stored in aliquots of 1 or 0.5 mL at −70° C. until analysis of APTT and PT.

The following compounds and doses were tested (each in groups of 8 rats) in adult rats:
Saline: (Negative Control)
Heparin: 0.7, 1.5, 3.5, and 7.0 mg/kg
Fragmin: 1.5, 3.5, 7.0 and 35 mg/kg
DF02: 3.5, 7.0, 35, 70, 105, 210, 350 and 700 mg/kg Juvenile Rat The following compounds and doses were tested (each in groups of 8 rats) in juvenile rats of age 14±1 days:
2. Saline: (Negative Control)
3. DF02: 7.0, 35, 70 and 105 mg/kg Bleeding time and coagulation parameters as measured in adult animals revealed that DF02 has a low anti-coagulant effect in rats. The potency of DF02 was less than that of the anticoagulants Heparin and Fragmin though, both of which had a profound effect on all parameters, the effect being directly correlated with the dose in question. The effect on PT was too weak to allow for comparative estimates.

Established bleeding time and coagulation parameters in juvenile animals, indicate that DF02 has a low anti-coagulant effect also in juvenile rats. The change in bleeding time and coagulation parameters in the juvenile rats are in the same range as in adult rats. As in the adult rats also in the juvenile rats the effect on PT was weak.

To further understand the difference in anticoagulant potency of the chemically modified heparin compounds, an estimation of equipotent relative doses was calculated (Table 4). The relation between the estimated equipotent relative doses was calculated with respect to effects on bleeding time and APTT as measured in the rat bleeding model. The normalization or comparator was set to unfractionated heparin see Table 4, below.

TABLE 4

| Relative Doses | DF02 | Heparin | Fragmin |
| --- | --- | --- | --- |
| Bleeding time (min) | 30-50 | 1 | 5 |
| APTT | 30-40 | 1 | 5 |

Table 5 below show the specific anti-coagulant activities of DF02 by anti-factor Xa and anti-factor IIa assays.

TABLE 5

| Drug substance | | Batch Results | | |
| --- | --- | --- | --- | --- |
| Property | Procedure | Batch 1 | Batch 2 | Batch 3 |
| Anticoagulant FIIa activity | Ph. Eur. (chromogenic assay) | 4.6 IU/mg | 5.0 IU/mg | 3.8 IU/mg |
| Anticoagulant activity anti-factor Xa | Ph. Eur. | 3.9 IU/mg | 4.9 IU/mg | 5.5 IU/mg |

For comparison, the corresponding value for Unfractionated Heparin (UFH) is at least 180 IU/mg.

EXAMPLE 5

Investigation of Rosetting and Cytoadherence in Malaria Infected Blood

DF02 has been investigated for effects in vitro malaria models, e.g. disruption of rosettes of infected and uninfected erythrocytes, and prevention or disruption of cytoadherence of infected erythrocytes to the endothelium. In both models DF02 has shown efficacy in a dose-dependent manner. DF02 demonstrated significant potency in field studies, where rosetting in fresh parasitized erythrocytes (pE) from patients with mild or complicated malaria were tested in vitro. DF02 has also been tested for blocking effects on merozoite invasion of erythrocytes in vitro. DF02 demonstrated equal potency per mg to heparin in this model.

Results

Figure 5:
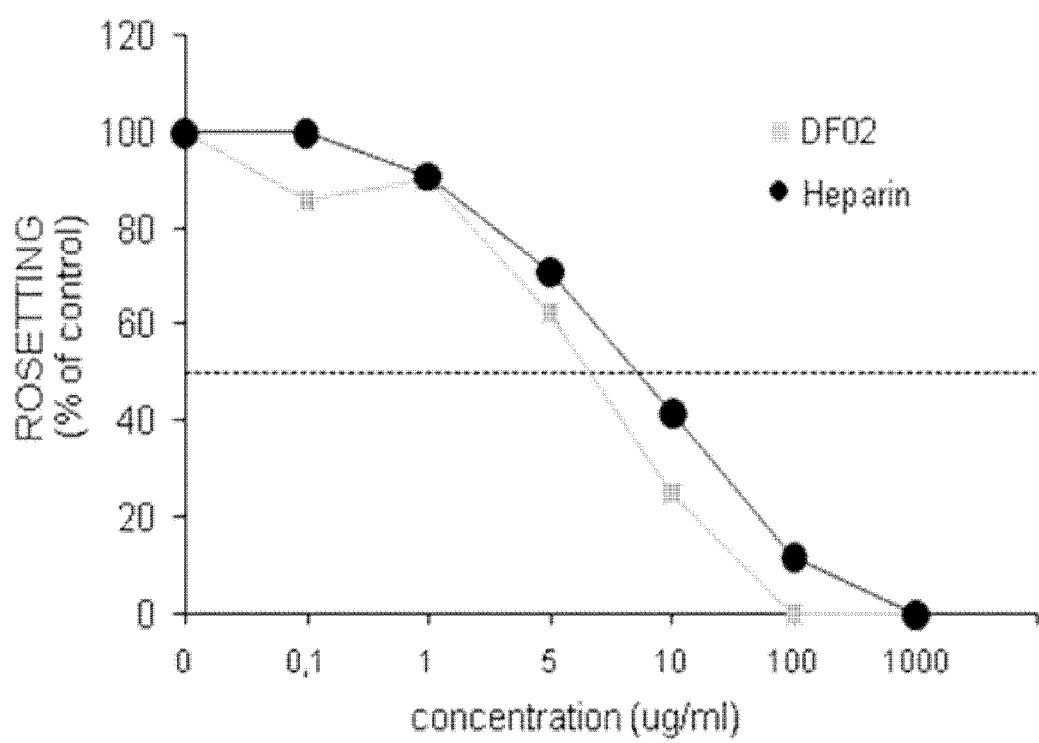
FIG. 5 shows how rosettes of the parasite FCR3S1.2 were disrupted by DF02 and heparin in a dose dependent manner.
Figure 6:
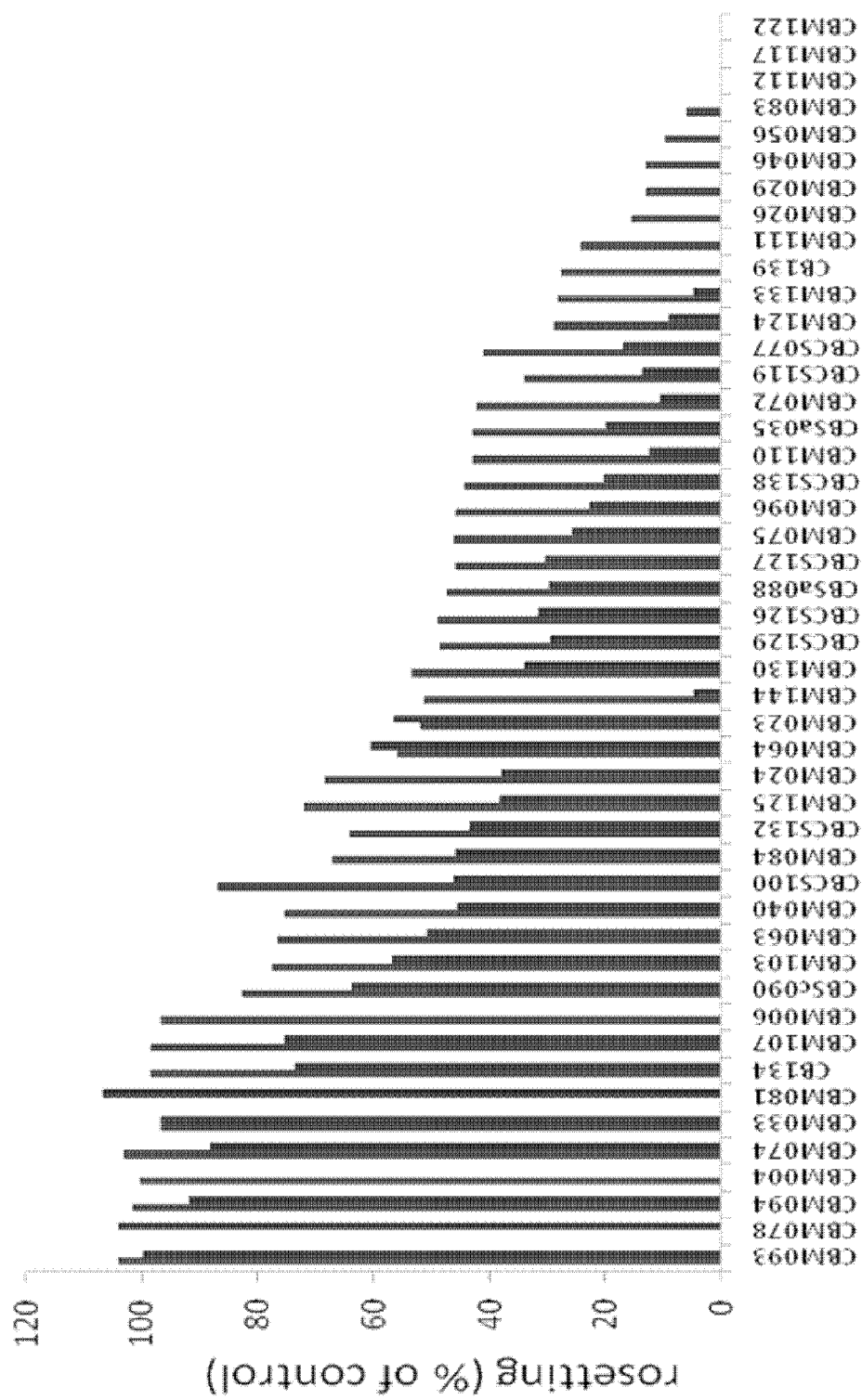
FIG. 6 shows how rosettes of fresh isolates of children with severe, complicated or mild malaria are sensitive to the treatment with DF02 (100 (dark bars) and 1000 (grey bars) µg/ml).
Figure 7:
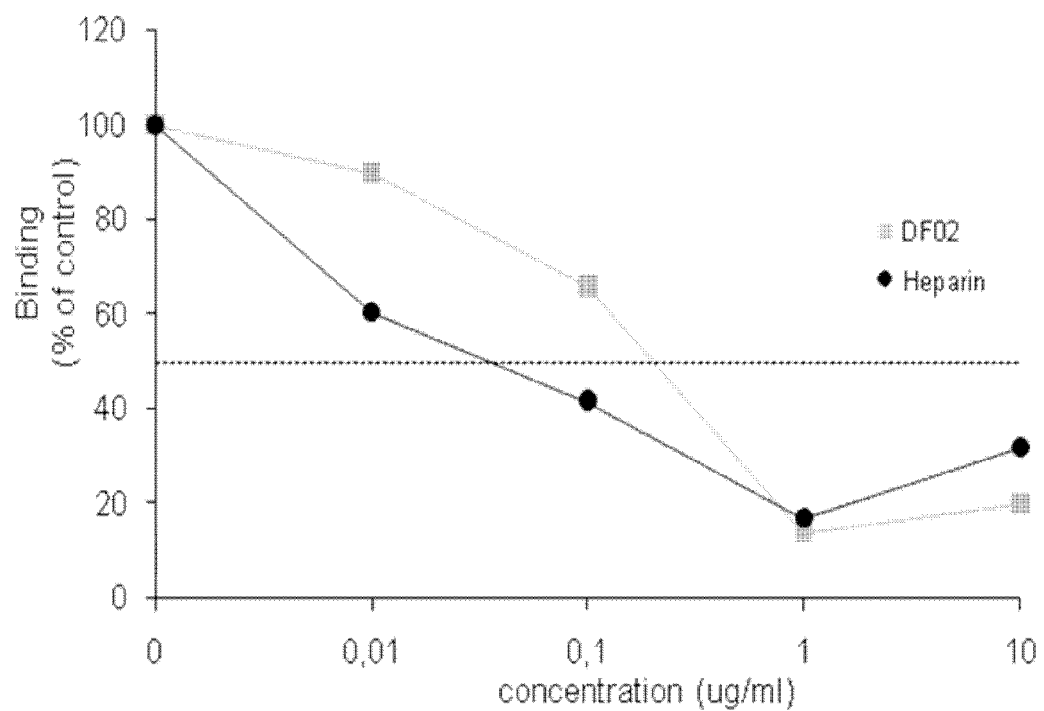
FIG. 7 shows cytoadherence disruption: binding of the pE of parasite FCR3S1.2 to endothelial cell can be inhibited or reversed by DF02 or heparin in a dose dependent manner.

A highly rosetting and multi-adhesive parasite clone (FCR3S1.2) as well as parasite isolates from severely ill patients have been tested for their sensitivity to DF02 in rosetting and cytoadherence assays. DF02 disrupts rosettes of many tested parasite cultures in a dose dependent manner and total or close to total disruption of rosettes was reached at 1000 µg/ml with some parasites (FIG. 5). The rosettes of clinical isolates were also sensitive to DF02. DF02 has further been investigated in the field. Forty-seven parasites from children with malaria showing the rosetting phenotype were treated with DF02. 91% of the rosetting blood samples collected from children with severe/complicated malaria showed 50% rosette disruption at the highest concentration tested (1000 μg /ml) (FIG. 6). The effect of DF02 on the binding of pE to endothelial cells (cytoadherence) has similarly been evaluated by dynamic incubation in order to mimic in vivo blood flow conditions. The direct effect on primary binding to endothelial cells was examined by adding pE together with DF02 simultaneously to the endothelium (cytoadherence blocking). Up to 80% of the binding of pE could be blocked by DF02 as compared with untreated samples. In order to test the efficiency of the DF02 to dislodge already bound pE from endothelium, pE were allowed to adhere to the endothelium, before incubation with the DF02 at different final concentrations (cytoadherence disruption). Cytoadherence disruption with DF02 resulted in up to 80% reduction of binding (FIG. 7). Some parasite cultures were more sensitive than others.

EXAMPLE 6

Effects of DF02 on Merozoite Invasion of Erythrocytes In Vitro

Figure 8:
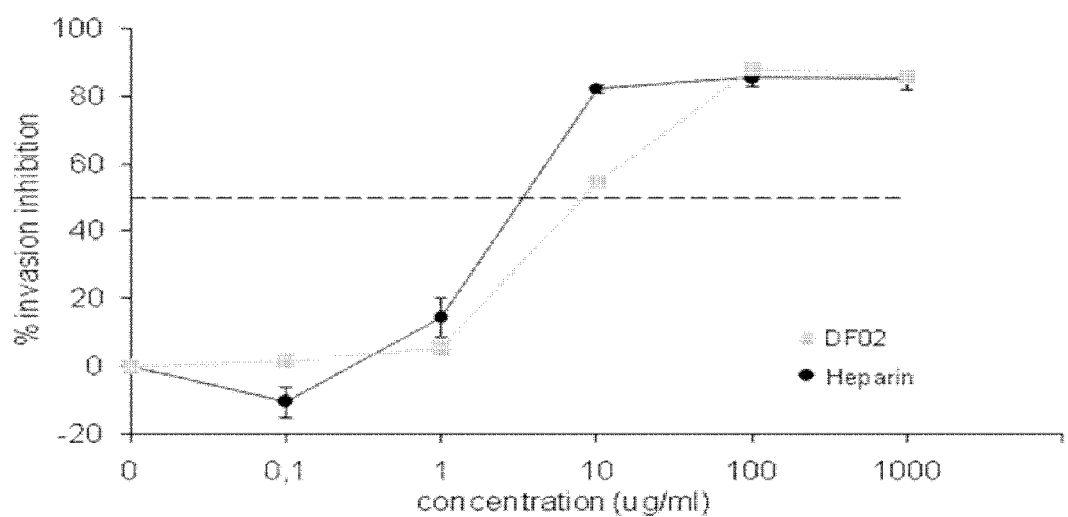
FIG. 8 demonstrates merozoite invasion of parasite FCR3S1.2 into fresh red blood cells can be inhibited by DF02 or heparin in a dose dependent manner.

The intra-erythrocyte lifecycle of P. falciparum is short and the pE burst every 48 h and released parasites have to reinvade fresh erythrocytes. Heparin has previously been demonstrated to inhibit continuous cultivation of P. falciparum in vitro by blocking merozoite invasion of erythrocytes. DF02 was therefore tested for their blocking effects on merozoite invasion of erythrocytes using an in vitro assay (FIG. 8). DF02 blocked merozoite invasion in a dose dependent manner and the inhibition was more than 80%. The inhibitory effects of the DF02 were found to be equal to those of standard heparin.

Method

The merozoite invasion inhibition assay was performed with chemically modified heparin and unfractionated heparin Mature pE (trophozoite) synchronized P. falciparum cultures with a parasitemia of 0.4% and a hematocrit of 2% were grown in micro-cultures (100 ul) in the presence of increasing concentrations of chemically modified heparin or unfractionated heparin at 37° C. for 24-30 h. In order to quantify the parasitemia, the samples were stained for 10 s with acridine orange and then analyzed using a FACS instrument from Becton Dickinson. A minimum of 50,000 cells per sample were collected.

Results

DF02 and standard heparin, were tested for their blocking effects on merozoite invasion of erythrocytes using an in vitro assay. DF02 blocked merozoite invasion in a dose-dependent manner and reached up to 80% inhibition. The inhibitory effects of the DF02 were found to be equal to those of standard heparin.

EXAMPLE 7

In Vivo Release of Sequestered Infected Erythrocytes

Figure 9:
FIG. 9 demonstrates that sequestration of P. falciparum-infected erythrocytes in the lungs of rats can be inhibited by the treatment with chemically modified heparin.

The efficacy of DF02 to release bound infected erythrocytes from lung micro-vessels into the blood circulation has been studied in vivo in the rat. DF02 demonstrated a release into the circulation of pE. In the rat model, an injection of the substance together with the pE blocked up to 80% of pE from binding in the lung of the rat. Similarly, when the pE were first injected, and allowed to bind in the microvasculature of the animals for 60 minutes, followed by an intravenous injection of DF02 up to 60% of the previously sequestered pE were found to be released by the treatment (FIG. 9).

Method

Human pE were cultivated in vitro and enriched to a parasitemia above 70%. Prior to injection into the animals, human infected erythrocytes were radioactively labeled with $^{99m}$Tc. The rats were anaesthetized and the labeled pE erythrocytes were injected intravenously into the tail vein. The treated rats were either co-injected with labeled pE together with different concentrations of the chemically modified heparin, or first injected with pE and, after 3 min, injected with different concentration of chemically modified heparin, unfractionated heparin, or dextran sulfate, whereas control animals were injected with labeled pE without DF02, heparin, or dextran sulfate. The distribution of the labeled cells was monitored using a gamma camera for 30 min. The relative amount of labeled cells sequestered in the lungs was calculated by comparing the activity of excised lungs to that of the whole animal.

Effect of Chemically Modified Heparin s on Sequestration of pE in Rats In Vivo

Studies of pE sequestration, including both rosetting and cytoadherence were performed in the rat. In this in vivo system pE of different strains and clones robustly adhere in the rat lungs in a PfEMP1– dependent manner. The system shows a sequestration-blocking effect of the chemically modified heparin DF02 on pE with a maximal 80% (approximately) average reduction of sequestration. Co-injection of uninfected labeled human erythrocytes with chemically modified heparin was compared with injection of labeled uninfected erythrocytes without chemically modified heparin. No difference was seen, and the overall amount retained was very low. Rats were also treated with chemically modified heparin s after the labeled pE had sequestered in order to study the capacity of the chemically modified heparin to release pE into circulation. Sequestration was reduced by approximately 50%.

EXAMPLE 8

Clinical Investigation of Sevuparin Sodium in Malaria Patients

A Phase I/II, Randomized, Open Label, Active Control, Parallel Assignment, Safety/Efficacy Study of Sevuparin/DF02 as an Adjunctive Therapy in Subjects Affected with Uncomplicated Falciparum Malaria.

P. falciparum infected erythrocytes (pEs) have the ability to sequestrate in the deep microvasculature in many of the vital organs. The sequestration property is involved in the generation of disease severity and pathology, through hampered blood flow, reduced oxygen delivery and consecutive tissue damage, and is based on the ability of trophozoite pEs to adhere to the vascular endothelium and to uninfected erythrocytes. The combined effect of endothelial and erythrocyte adhesion of pEs, is the pivotal mechanism leading to the obstruction of the microvasculature, and thereby the clinical symptoms of severe malaria.

Sevuparin sodium is administered as an i.v. infusion in combination with atovaquone/proguanil (Malanil®) as antimalarial treatment to female and male subjects (18 to 65 years of age) affected with uncomplicated malaria. A dose escalation part (part 1) is followed by an open labelled, randomized comparison of treatment with sevuparin sodium and Malanil® versus Malanil® alone (part 2). Sevuparin sodium is administered to each patient 4 times a day and atovaquone/proguanil (Malanil®) is administered to each patient according to its labelled indication. The study arms are sevuparin sodium in combination with atovaquone/proguanil (Malanil®) and atovaquone/proguanil (Malanil®) alone as control.

Method

Parasite clearance curves and sequential peripheral blood parasite staging of DF02 treated patients are compared with the control group. Cytoadherence and thus sequestration of pEs containing the more mature forms of the parasite is affected by DF02, a temporary rise in parasitemia and appearance of more mature stages of the parasite in the peripheral blood. The clearance curves in relation to the peripheral blood staging are modeled using stage distribution, proportion of stage specific sequestration and stage specific parasite clearance through quinine as parameters. A similar approach has been trialed in the evaluation of levamisole as anti-adhesive adjuvant therapy in falciparum malaria (Dondorp et al. J Infect Dis 2007; 196:460-6). Differences in sequestration between DF02 treated patients and the control group are evaluated by comparing the integrated numbers (in parasites per microliter) and parasitemia (in percentages) of trophozoite- and schizont-stage parasites seen in the peripheral blood over time up to 72 h, determined as the area under the time-parasitemia curve. The well-defined morphological stages of the parasite consist of the following: tiny rings, small rings, large rings, early trophozoites, midtrophozoites, late trophozoites, and schizonts [Silamut K, et al. Am J Pathol 1999; 155:395-410]. The parasite asexual-stage ages (from merozoite invasion) bordering the morphological stages, as assessed by in vitro culture, are, respectively, 12, 17, 22, 28, 37, and 42 h. A cohort of large-ring forms on admission evolves to the early trophozoite stage 6 h later. Other matching cohorts include tiny rings on admission and small and large rings combined after 12 h, small rings on admission and large rings after 6 h, early trophozoites after 12 h and midtrophozoites after 18 h, and large rings on admission and either midtrophozoites after 12 h or late trophozoites after 18 h. Assessment of peripheral blood slides is performed by 2 independent microscopists, who are blinded to the study drug allocation.

The invention claimed is:

1. Chemically modified heparin having an antifactor IIa activity and an antifactor Xa activity, wherein the antifactor IIa activity is up to 10 IU/mg and the antifactor Xa activity of up to 10 IU/mg, wherein the chemically modified heparin has a weight average molecular weight from about 6.5 to about 9.5 kDa, wherein the polysaccharide chains:
   (i) retain at least 90% of the sulfate groups of the corresponding native heparin;
   (ii) have a reduction in chemically intact pentasaccharide sequences providing an antithrombin mediated anticoagulant effect, when compared to the polysaccharide chains of native heparin;
   (iii) have a reduction in unsulfated iduronic and/or glucuronic acid units when compared to native heparin; and
   wherein the predominant disaccharide of the polysaccharide has the chemical structure:

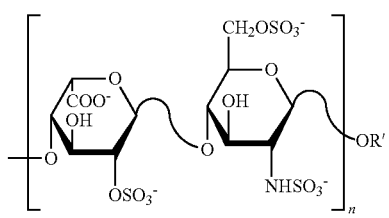

wherein R' is a threonate residue and n is an integer of from 2 to 25, such that it comprises from 2 to 25 disaccharide units corresponding to molecular weights from 1.2 to 15 kDa.

2. Chemically modified heparin according to claim 1, wherein the predominantly occurring polysaccharide chains have from 6 to 16 disaccharide units with molecular weights from about 3.6 to about 9.6 kDa.

3. Chemically modified heparin according to claim 1, wherein at least 30% of the polysaccharide chains have a molecular weight of at least 8 kDa.

4. Chemically modified heparin according to claim 1, comprising glycol-split residues of the chemical structure:

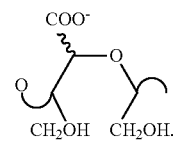

5. Chemically modified heparin according to claim 1, wherein 3-15% of the polysaccharide chains have a molecular mass of at least 15 kDa.

6. Chemically modified heparin according to claim 1, wherein 25-47% of the polysaccharide chains have a molecular mass of at least 9 kDa.

7. Chemically modified heparin according to claim 1, wherein 40-60% of the polysaccharide chains have a molecular mass of at least 7 kDa.

8. Chemically modified heparin according to claim 1, wherein 60-80% of the polysaccharide chains have a molecular mass of at least 5 kDa.

9. Chemically modified heparin according to claim 1, wherein at least 85% of the polysaccharide chains have a molecular mass of at least 3 kDa.

10. Chemically modified heparin according to claim 1, wherein at least 95% of the polysaccharide chains have a molecular mass of at least 2 kDa.

11. A method for the treatment of malaria, comprising the administration to a patient in need of such treatment, a therapeutically effective amount of a chemically modified heparin according to claim 1.

12. A pharmaceutical composition comprising a therapeutically effective amount of a chemically modified heparin according to claim 1, together with a pharmaceutically and pharmacologically acceptable carrier.

13. A method of preparing chemically modified heparin having an antifactor II activity and an antifactor Xa activity, wherein the antifactor IIa activity is up to 10 IU/mg and the antifactor Xa activity is up to 10 IU/mg, and the chemically modified heparin having a weight average molecular weight from about 6.5 to about 9.5 kDa, the method comprising the consecutive steps of:
   (a) selectively oxidizing unfractionated heparin by subjecting it to an oxidizing agent capable of oxidizing non-sulfated saccharides residues;
   (b) reducing the resulting oxidized saccharide residue; and
   (c) depolymerizing the heparin chains by hydrolysis at an acidic pH of from about 3 to about 4.

14. The method according to claim 13, further comprising at least one step of eliminating remaining oxidizing agent.

15. The method according to claim 14, wherein at least one elimination step comprises removing reduced forms of the oxidizing agent.

16. The method according to claim 13 comprising a step of eliminating any remaining oxidizing agent and removing reduced forms of oxidizing agent between the reduction step (b) and the depolymerization step (c).

17. The method according to claim 16, comprising depolymerizing the heparin chains by hydrolysis at an acidic pH from about 3.0 to about 3.5.

18. The method according to claim 14, wherein the elimination step comprises adding an alcohol in an amount sufficient for the chemically modified heparin to precipitate.

19. The method according to claim 13, whereby depolymerization is performed at a temperature of at least 20° C.

20. The method according to claim 13, whereby the chemically modified heparin is enriched with polysaccharide chains having a molecular weight of about from 5.5 to about 10.5 kDa.

21. The method according to claim 13, whereby unsulfated iduronic and/or unsulfated glucuronic acids are selectively oxidized by a periodate compound.

22. A chemically modified heparin manufactured by a method according to claim 19, wherein the chemically modified heparin comprises polysaccharide chains where the predominant disaccharide of the polysaccharide has the chemical structure:

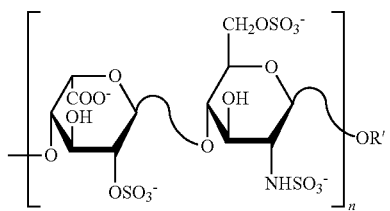

wherein R' is a threonate residue and n is an integer of from 2 to 25, such that it comprises from 2 to 25 disaccharide units corresponding to molecular weights from 1.2 to 15 kDa.

23. A combination comprising a chemically modified heparin according to claim 1, and another medicament for the treatment of malaria.

24. A combination according to claim 23, wherein the other medicament is atovaquone/proguanil.

25. A combination according to claim 23, wherein the other medicament is artesunate.

26. The chemically modified heparin according to claim 1, wherein the chemically modified heparin has, in a $^1$H-NMR spectrum, no unidentified signals in the ranges 0.10-2.00 ppm, 2.10-3.10 ppm and 5.70-8.00 ppm larger than 4 percent when compared to the height of the signal present in native heparin at 5.42 ppm.

27. The chemically modified heparin according to claim 2, wherein the chemically modified heparin has, in a $^1$H-NMR spectrum, no unidentified signals in the ranges 0.10-2.00 ppm, 2.10-3.10 ppm and 5.70-8.00 ppm larger than 4 percent when compared to the height of the signal present in native heparin at 5.42 ppm.

28. The chemically modified heparin according to claim 22, wherein the chemically modified heparin has, in a $^1$H-NMR spectrum, no unidentified signals in the ranges 0.10-2.00 ppm, 2.10-3.10 ppm and 5.70-8.00 ppm larger than 4 percent when compared to the height of the signal present in native heparin at 5.42 ppm.

29. The method according to claim 13, wherein the chemically modified heparin comprises polysaccharide chains where the predominant disaccharide of the polysaccharide has the chemical structure:

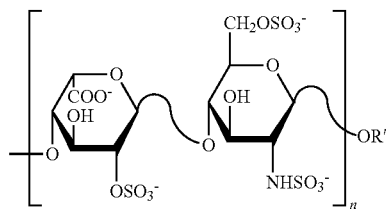

wherein R' is a threonate residue and n is an integer of from 2 to 25, such that it comprises from 2 to 25 disaccharide units corresponding to molecular weights from 1.2 to 15 kDa.

* * * * *